US 9,902,672 B2

(12) United States Patent
Wang et al.

(10) Patent No.: US 9,902,672 B2
(45) Date of Patent: *Feb. 27, 2018

(54) METHOD FOR PRODUCING HYDROFLUOROOLEFIN

(71) Applicant: ASAHI GLASS COMPANY, LIMITED, Chiyoda-ku (JP)

(72) Inventors: Xu Wang, Chiyoda-ku (JP); Shinji Terazono, Chiyoda-ku (JP); Masahiro Kanda, Chiyoda-ku (JP); Satoshi Kawaguchi, Chiyoda-ku (JP); Mitsugu Kasagawa, Chiyoda-ku (JP)

(73) Assignee: ASAHI GLASS COMPANY, LIMITED, Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/425,283

(22) Filed: Feb. 6, 2017

(65) Prior Publication Data

US 2017/0144949 A1   May 25, 2017

Related U.S. Application Data

(63) Continuation of application No. PCT/JP2015/073749, filed on Aug. 24, 2015.

(30) Foreign Application Priority Data

Aug. 25, 2014   (JP) ................................. 2014-170503

(51) Int. Cl.
*C07C 17/23* (2006.01)
*C07C 17/354* (2006.01)
(Continued)

(52) U.S. Cl.
CPC ............ *C07C 17/23* (2013.01); *C07C 17/354* (2013.01); *C07C 21/18* (2013.01); *B01J 23/40* (2013.01);
(Continued)

(58) Field of Classification Search
CPC ...................................................... C07C 17/23
See application file for complete search history.

(56) References Cited

U.S. PATENT DOCUMENTS 7,795,481 B2 *   9/2010   Nappa .................... B01J 23/58
570/136
8,318,991 B2 *  11/2012   Sugimoto ............... C07C 17/23
570/153

(Continued)

FOREIGN PATENT DOCUMENTS

CA   2015247 A1 * 10/1990 ............. C07C 17/23
JP   1-287044   11/1989
(Continued)

OTHER PUBLICATIONS

Huang (Huang, C-C. et al. "Effect of surface acidic oxides of activated carbon on adsorption of ammonia" Journal of Hazardous Materials 159 (2008) pp. 523-552).*

(Continued)

*Primary Examiner* — Medhanit W Bahta
(74) *Attorney, Agent, or Firm* — Oblon, McClelland, Maier & Neustadt, L.L.P.

(57) ABSTRACT

A hydrofluoroolefin is produced by reacting a chlorofluoroolefin with hydrogen in the presence of a platinum group metal catalyst supported on a carbon carrier to obtain a hydrofluoroolefin. The chlorofluoroolefin is represented by formula (1): CZX=CClY, where X is F or Cl, Y is F, Cl or H, and Z is F or $CF_3$. The hydrofluoroolefin is represented by formula (2): CZX'=CHY', where X' is F when X is F, or X' is H when X is Cl, Y' is F when Y is F, or Y' is H when Y is Cl or H, and Z is the same as Z in the formula (1). The carbon carrier has acidic functional groups, and the total acidic functional group amount in the carbon carrier is at most 50 µmol/g.

19 Claims, 2 Drawing Sheets

(51) Int. Cl.
| | |
|---|---|
| C07C 21/18 | (2006.01) |
| B01J 23/46 | (2006.01) |
| B01J 23/44 | (2006.01) |
| B01J 23/72 | (2006.01) |
| B01J 23/40 | (2006.01) |
| B01J 23/42 | (2006.01) |
| B01J 23/50 | (2006.01) |
| B01J 23/48 | (2006.01) |
| B01J 23/52 | (2006.01) |
| C07B 61/00 | (2006.01) |

(52) U.S. Cl.
CPC ............. *B01J 23/42* (2013.01); *B01J 23/44* (2013.01); *B01J 23/46* (2013.01); *B01J 23/462* (2013.01); *B01J 23/464* (2013.01); *B01J 23/468* (2013.01); *B01J 23/48* (2013.01); *B01J 23/50* (2013.01); *B01J 23/52* (2013.01); *B01J 23/72* (2013.01); *C07B 61/00* (2013.01)

(56) References Cited

U.S. PATENT DOCUMENTS

| | | |
|---|---|---|
| 2007/0299287 A1 | 12/2007 | Hedrick |
| 2008/0300432 A1 | 12/2008 | Hedrick et al. |
| 2011/0319679 A1 | 12/2011 | Takagi et al. |
| 2012/0302804 A1 | 11/2012 | Sakyu et al. |
| 2013/0131402 A1* | 5/2013 | Millefanti ............... B01J 21/18 570/156 |

FOREIGN PATENT DOCUMENTS

| | | |
|---|---|---|
| JP | 2-286635 | 11/1990 |
| JP | 2526661 | 8/1996 |
| JP | 2008-510831 | 4/2008 |
| WO | WO 2008/060614 A2 | 5/2008 |
| WO | WO 2008/060614 A3 | 5/2008 |
| WO | WO 2011/102167 A1 | 8/2011 |
| WO | WO 2011/162340 A1 | 12/2011 |
| WO | WO 2012/000853 A1 | 1/2012 |

OTHER PUBLICATIONS

Meng, B-C. et al. "Selective Liquid-phase Hydrodechlorination of Chlorotrifluoroethylene over Palladium-Supported Catalysts: Activity and Deactivation" Catal Lett (2010) 138:68-75 (Year: 2010).*
International Search Report dated Oct. 27, 2015 in PCT/JP2015/073749, filed on Aug. 24, 2015.

* cited by examiner

METHOD FOR PRODUCING HYDROFLUOROOLEFIN

TECHNICAL FIELD

The present invention relates to a method for producing a hydrofluoroolefin.

BACKGROUND ART 2,3,3,3-Tetrafluoropropene ($CF_3CF=CH_2$) (hereinafter sometimes referred to as "HFO-1234yf), which contains no chlorine, is useful as an alternative to Freon such as a chlorofluorocarbon to be used as a refrigerant, etc.

As a method for producing HFO-1234yf, a method may be mentioned in which 1,1-dichloro-2,2,3,3,3-pentafluoropropane ($CF_3CF_2CHCl_2$) (hereinafter sometimes referred to as "HCFC-225ca") is subjected to dehydrofluorination to obtain 1,1-dichloro-2,3,3,3-tetrafluoropropene ($CF_3CF=CCl_2$) (hereinafter sometimes referred to as "CFO-1214ya"), and the obtained CFO-1214ya is reduced by reaction with hydrogen to obtain HFO-1234yf.

As a method of reducing CFO-1214ya to obtain HFO-1234yf, for example, the following method (i) disclosed in Patent Document 1 may be mentioned. (i) A method of subjecting CFO-1214ya and a hydrogen gas to a reaction represented by the following formula (6) in the presence of a palladium catalyst supported on alumina, at from 100 to 400° C., preferably from 125 to 350° C.:

$$CF_3CF=CCl_2+2H_2 \rightarrow CF_3CF=CH_2+2HCl \quad (6)$$

However, by the reaction represented by the above formula (6), 3,3,3-trifluoropropene ($CF_3CH=CH_2$) (hereinafter sometimes referred to as "HFO-1243zf") which is an over-reduced product forms as a by-product. HFO-1243zf has a boiling point close to that of the aimed HFO-1234yf, and is thereby hardly separated and removed by subsequent distillation. Accordingly, HFO-1243zf will remain as an impurity in HFO-1234yf obtainable by distillation, and a separation and purification step is additionally required to obtain a high purity product.

Further, Patent Document 2 discloses the following method (ii) as a method of carrying out a reduction reaction similarly. (ii) A method of reacting $RfCF=CX_2$ (wherein Rf is a $C_{1-10}$ fluoroalkyl group, and X is chlorine, bromine or iodine) with hydrogen at from 5 to 200° C. in the presence of a palladium catalyst supported on activated carbon to obtain $RfCF=CH_2$.

However, in the method (ii) also, $RfCH=CH_2$ which is an over-reduced product forms as a by-product together with the aimed $RfCF=CH_2$. For example, in a case where Rf is $CF_3-$, that is, in a case where the aimed product is HFO-1234yf, the over-reduced product is hardly separated from the aimed product by distillation in the same manner as the method (i).

Further, as a method for reducing chlorine in a chlorofluoroolefin, Patent Document 3 discloses the following method (iii). (iii) A method of subjecting chlorotrifluoroethylene and a hydrogen gas to a reaction represented by the following formula (10) in the presence of a palladium catalyst supported on activated carbon at from 100 to 350° C., preferably from 200 to 250° C.:

$$CF_2=CClF+H_2 \rightarrow CF_2=CHF+HCl \quad (10)$$

Further, Patent Document 4 discloses the following method (iv).

(iv) A method of subjecting 1,2-dichlorodifluoroethylene and a hydrogen gas to a reaction represented by the following formula (11) in the presence of a palladium catalyst supported on activated carbon at from 150 to 600° C., preferably from 200 to 400° C.:

$$CClF=CClF+2H_2 \rightarrow CHF=CHF+2HCl \quad (11)$$
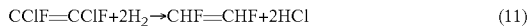

However, in the methods (iii) and (iv) also, an over-reduced product will form as a by-product, whereby the impurity of the aimed product will decrease.

PRIOR ART DOCUMENTS

Patent Documents

Patent Document 1: WO2008/060614
Patent Document 2: JP-A-H$_2$-286635
Patent Document 3: WO2012/000853
Patent Document 4: JP-A-H$_1$-287044

DISCLOSURE OF INVENTION

Technical Problem

It is an object of the present invention to provide a method for producing a hydrofluoroolefin, by a reaction of replacing chlorine atoms in a material chlorofluoroolefin with hydrogen atoms to produce a hydrofluoroolefin, wherein formation of an over-reduced product having not only chlorine atoms but also fluorine atoms replaced by hydrogen atoms, as a by-product, is suppressed.

Solution to Problem

The present invention provides the following [1] to [15].

[1] A method for producing a hydrofluoroolefin, which comprises reacting a chlorofluoroolefin represented by the following formula (1) with hydrogen in the presence of a platinum group metal catalyst supported on a carbon carrier, to obtain a hydrofluoroolefin represented by the following formula (2), wherein the total acidic functional group amount in the carbon carrier is at most 50 μmol/g:

$$CZX=CClY \quad (1)$$

wherein X is a fluorine atom or a chlorine atom, Y is a fluorine atom, a chlorine atom or a hydrogen atom, and Z is a fluorine atom or $CF_3$;

$$CZX'=CHY' \quad (2)$$

wherein X' is a fluorine atom when X is a fluorine atom, or X' is a hydrogen atom when X is a chlorine atom, Y' is a fluorine atom when Y is a fluorine atom, or Y' is a hydrogen atom when Y is a chlorine atom or a hydrogen atom, and Z is the same as Z in the formula (1).

[2] The method for producing a hydrofluoroolefin according to [1], wherein the platinum group metal catalyst is composed of palladium, a palladium alloy, rhodium or platinum.

[3] The method for producing a hydrofluoroolefin according to [1], wherein the platinum group metal catalyst is composed of an alloy of a platinum group element and gold.

[4] The method for producing a hydrofluoroolefin according to [3], wherein the platinum group metal catalyst is composed of an alloy of palladium and gold.

[5] The method for producing a hydrofluoroolefin according to any one of [1] to [4], wherein the total acidic functional group amount in the carbon carrier is at most 30 μmol/g.

[6] The method for producing a hydrofluoroolefin according to any one of [1] to [4], wherein the total acidic functional group amount in the carbon carrier is at most 20 µmol/g.

[7] The method for producing a hydrofluoroolefin according to any one of [1] to [6], wherein the carbon carrier has a specific surface area of from 10 to 2,000 m$^2$/g.

[8] The method for producing a hydrofluoroolefin according to any one of [1] to [7], wherein the amount of the platinum group metal catalyst supported is from 0.1 to 10 mass % based on the carbon carrier.

[9] The method for producing a hydrofluoroolefin according to any one of [1] to [8], wherein the chlorofluoroolefin and hydrogen are introduced to a catalyst layer of a tubular reactor packed with the carbon carrier supporting the catalyst, and reacted in a gaseous phase.

[10] The method for producing a hydrofluoroolefin according to [9], wherein the tubular reactor has a gas introduction part and a gas discharge part, and the chlorofluoroolefin and hydrogen are introduced to the gas introduction part and hydrogen is introduced from at least one point between the gas introduction part and the gas discharge part.

[11] The method for producing a hydrofluoroolefin according to [9] or [10], wherein the reaction is carried out while the maximum temperature of the catalyst layer is controlled to be at most 130° C.

[12] The method for producing a hydrofluoroolefin according to any one of [9] to [11], wherein the proportion of hydrogen to the chlorofluoroolefin introduced to the catalyst layer is from 0.1 to 0.7 as represented by the ratio (H$_2$/Cl) of the total number of moles of hydrogen to the number of moles of chlorine atoms in the chlorofluoroolefin.

[13] The method for producing a hydrofluoroolefin according to any one of [1] to [8], wherein the chlorofluoroolefin and hydrogen are reacted in a liquid phase in the presence of the carbon carrier supporting the catalyst.

[14] The method for producing a hydrofluoroolefin according to any one of [1] to [13], wherein the chlorofluoroolefin is at least one member selected from the group consisting of chlorotrifluoroethylene, trans-1,2-dichloro-1,2-difluoroethylene, cis-1,2-dichloro-1,2-difluoroethylene, 1,1-dichloro-2,3,3,3-tetrafluoropropene and 1-chloro-2,3,3,3-tetrafluoropropene.

[15] The method for producing a hydrofluoroolefin according to any one of [1] to [13], wherein 2,3,3,3-tetrafluoropropene is produced from 1,1-dichloro-2,3,3,3-tetrafluoropropene.

Advantageous Effects of Invention

According to the production method of the present invention, formation of an over-reduced product having not only chlorine atoms but also fluorine atoms in a material chlorofluoroolefin replaced with hydrogen atoms as a by-product is suppressed, whereby the aimed hydrofluoroolefin can be obtained easily with high purity.

DESCRIPTION OF EMBODIMENTS

[Method for Producing Hydrofluoroolefin]

Figure 1:
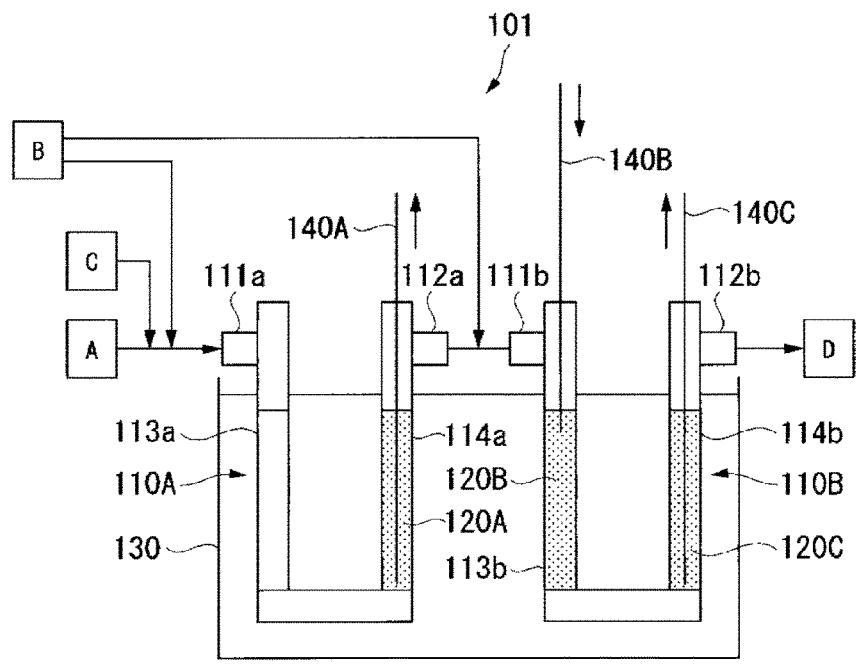
FIG. 1 is a view schematically illustrating a reaction apparatus used in Examples.

The present invention provides a method for producing a hydrofluoroolefin, which comprises reacting a chlorofluoroolefin represented by the above formula (1) with hydrogen in the presence of a platinum group metal catalyst supported on a carbon carrier, to obtain a hydrofluoroolefin represented by the above formula (2).

Further, the carbon carrier supporting the catalyst used in the production method is a carbon carrier having a total acidic functional group amount of at most 50 µmol/g.

(Material and Reaction Product)

<Chlorofluoroolefin>

The chlorofluoroolefin which is one of the materials in the present invention is a compound represented by the above formula (1). Among the chlorofluoroolefins represented by the formula (1), in that a formed product is expected as an environmentally friendly alternative refrigerant having a high refrigerating efficiency, preferred is chlorotrifluoroethylene, trans-1,2-dichloro-1,2-difluoroethylene, cis-1,2-dichloro-1,2-difluoroethylene, CFO-1214ya or 1-chloro-2,3,3,3-tetrafluoropropene (hereinafter sometimes referred to as "HCFO-1224yd"). Further, a mixture of CFO-1214ya and HCFO-1224yd is also preferred.

Hereinafter, a trans-form of geometrical isomers will be represented by adding the prefix (E) to a compound name or a chemical formula, and a cis-form is represented by adding the prefix (Z) to a compound name or a chemical formula.

Chlorotrifluoroethylene can be produced by dechlorination of 1,1,2-trichloro-1,2,2-trifluoroethane or heat decomposition of chlorodifluoromethane and dichlorofluoromethane.

(E)-1,2-dichloro-1,2-difluoroethylene and (Z)-1,2-dichloro-1,2-difluoroethylene can be produced by heat decomposition of dichlorofluoromethane.

CFO-1214ya can be produced by a known method. For example, a method of bringing HCFC-225ca into contact with an aqueous alkali solution in the presence of a phase transfer catalyst to conduct dehydrofluorination may be mentioned. For the reaction, dichloropentafluoropropane (hereinafter sometimes referred to as "HCFC-225") containing HCFC-225ca may be used, and only HCFC-225ca in HCFC-225 is selectively subjected to dehydrofluorination by the phase transfer catalyst. After the reaction, CFO-1214ya can be separated and recovered by a known method such as distillation.

The above HCFC-225 containing HCFC-225ca can be produced by reacting tetrafluoroethylene and dichlorofluoromethane in the presence of a catalyst such as aluminum chloride. HCFC-225 obtained by the reaction contains as the main component HCFC-225ca and 1,3-dichloro-1,2,2,3,3-pentafluoropropane (CHClFCF$_2$CClF$_2$) (hereinafter sometimes referred to as "HCFC-225cb") and further contains a small amount of 2,2-dichloro-1,1,3,3,3-pentafluoropropane (CHF$_2$CCl$_2$CF$_3$, hereinafter sometimes referred to as "HCFC-225aa"), 2,3-dichloro-1,1,2,3,3-pentafluoropropane (CHF$_2$CClFCClF$_2$, hereinafter sometimes referred to as "HCFC-225bb") and the like.

As the HCFC-225 containing HCFC-225ca, a commercial product may be used. As a commercial product, ASAHIKLIN (trademark) AK225 (manufactured by Asahi Glass Company, Limited, a mixture comprising 48 mol % of HCFC-225ca and 52 mol % of HCFC-225cb, hereinafter referred to as "AK225") may, for example, be mentioned.

The phase transfer catalyst is preferably tetrabutylammonium bromide (TBAB).

HCFO-1224yd is formed as an intermediate when CFO-1214ya and hydrogen are reacted to obtain HFO-1234yf.

<Reaction Product>

The aimed reaction product obtainable by the production method of the present invention is a compound represented by the above formula (2). X', Y' and Z in the above formula (2) correspond to X, Y and Z in the chlorofluoroolefin represented by the above formula (1) which is one of the materials.

When X in the above formula (1) is a fluorine atom, X' is a fluorine atom. When X is a chlorine atom, X' is a hydrogen atom.

When Y in the above formula (1) is a fluorine atom, Y' is a fluorine atom. When Y is a chlorine atom or a hydrogen atom, Y' is a hydrogen atom.

Z in the above formula (1) is the same as Z in the above formula (1).

For example, in a case where the material chlorofluoroolefin is chlorotrifluoroethylene, trifluoroethylene obtained by a reaction represented by the following formula (3) is the aimed reaction product.

$$CFCl=CF_2+H_2 \rightarrow CHF=CF_2+HCl \tag{3}$$

In a case where the material chlorofluoroolefin is 1,2-dichloro-1,2-difluoroethylene, 1,2-difluoroethylene obtained by reactions represented by the following formulae (4) and (5) is the aimed reaction product.

$$(E)\text{-}CFCl=CFCl+2H_2 \rightarrow (E)\text{-}CHF=CHF+2HCl \tag{4}$$

$$(Z)\text{---}CFCl=CFCl+2H_2 \rightarrow (Z)\text{---}CHF=CHF+2HCl \tag{5}$$

In a case where the material chlorofluoroolefin is CFO-1214ya, HCFO-1224yd obtained by a reaction represented by the following formula (6) is the aimed reaction product.

$$CF_3CF=CCl_2+2H_2 \rightarrow CF_3CF=CH_2+2HCl \tag{6}$$

In a case where the material chlorofluoroolefin is HCFO-1224yd, HFO-1234yf obtained by a reaction represented by the following formula (7) is the aimed reaction product.

$$CF_3CF=CHCl+H_2 \rightarrow CF_3CF=CH_2+HCl \tag{7}$$

(Catalyst)

The catalyst in the present invention is a platinum group metal catalyst supported on a carbon carrier having acidic functional groups in a total acidic functional group amount of at most 50 µmol/g.

<Platinum Group Metal Catalyst>

The platinum group metal catalyst may be palladium, rhodium, platinum, iridium, ruthenium or osmium. The platinum group metal may be used alone or in combination of two or more.

In a case where two or more types of platinum group metals are used as the catalyst, the platinum group metals used may be in the form of a mixture or an alloy. The alloy may, for example, be a palladium/platinum alloy.

Among such platinum group metal catalysts, in view of higher activity, preferred is palladium, a palladium alloy, rhodium or platinum, more preferred is palladium or a palladium alloy.

The platinum group metal catalyst may be a catalyst composed of an alloy of a platinum group element and a metal element other than the platinum group element, with a view to improving the durability of the catalyst and suppressing formation of an over-reduced product as a by-product. The metal element other than the platinum group element may, for example, be gold, iron, cobalt, nickel, bismuth or copper. The metal element other than the platinum group element is particularly preferably gold. Such a metal element other than the platinum group element may be used alone or in combination of two or more. An alloy catalyst containing a metal element other than the platinum group element is particularly preferably a catalyst composed of an alloy of palladium and gold.

In the catalyst composed of an alloy of the platinum group element and the metal element other than the platinum group element, the proportion of the metal element other than the platinum group element is preferably from 0.01 to 50 parts by mass per 100 parts by mass of the platinum group element.

<Carbon Carrier>

The carbon carrier in the present invention is a carbon carrier having acidic functional groups in a total acidic functional group amount of at most 50 µmol/g.

By using such a carbon carrier having a total acidic functional group amount of at most 50 µmol/g, formation of an over-reduced product as a by-product is suppressed.

The total acidic functional group amount in the carbon carrier is preferably at most 30 µmol/g, more preferably at most 20 µmol/g, further preferably at most 10 µmol/g, with a view to further suppressing formation of an over-reduced product as a by-product.

In the present invention, the total acidic functional group amount in the carbon carrier is determined as follows.

The total acidic functional group amount in the carbon carrier is determined in accordance with Boehm method (described in detail in H. P. Boehm, Adzan. Catal, 16, 179 (1966)).

Specifically, 30 mL of a sodium hydroxide solution (0.018 mol/L) is added to 2 g of a sample, followed by stirring at 500 rpm for 2 hours, and the mixture is left to stand for 24 hours. 24 Hours later, stirring is conducted further for 30 minutes, followed by separation by filtration. To 15 mL of the obtained filtrate, 0.01 mol/L hydrochloric acid is dropwise added, and hydrochloric acid titer b (mL) when the pH becomes 7.0 is measured.

Further, as a blank test, 0.01 mol/L hydrochloric acid is dropwise added to 15 mL of the above aqueous sodium hydroxide solution (0.018 mol/L), and the hydrochloric acid titer a (mL) when the pH becomes 7.0 is measured.

The total acid functional group amount (µmol/g) is calculated in accordance with the following formula (8).

$$\text{Total acidic functional group amount}(\mu mol/g)=\{(a-b)\times 0.01\times 1000\}/\{m\times(15/30)\} \tag{8}$$

a: hydrochloric acid titer (mL) in blank test
b: hydrochloric acid titer (ml) when the sample is reacted
m: mass (g) of sample The acidic functional groups in the carbon carrier may be removed by a known method such as heat treatment. Accordingly, even if the material carbon carrier has a total acidic functional group amount exceeding 50 µmol/g, such a carbon carrier may be used as the carbon carrier of the present invention after subjected to heat treatment in an inert gas atmosphere of e.g. nitrogen at from 350 to 1,200° C. to reduce the total acidic functional group amount to be a desired amount or smaller.

The heat treatment of the carbon carrier may be conducted before the platinum group metal catalyst is supported or may be conducted after the platinum group metal catalyst is supported. However, a chemical reagent used in a process to let the platinum group metal catalyst be supported may act on the activated carbon to increase the acidic functional groups, and accordingly the heat treatment of the carbon carrier is carried out preferably after the platinum group metal catalyst is supported.

The acidic functional group in the carbon carrier is a functional group which neutralizes the sodium hydroxide solution in measurement by the above Boehm method and is considered to be a carboxy group, a group capable of being converted to a carboxy group, a phenolic hydroxy group, a group capable of being converted to a phenolic hydroxy group, etc. Particularly, the acidic functional group in the carbon carrier is considered to be a carboxy group, a group capable of being converted to a carboxy group, a phenolic hydroxy group or a group capable of being converted to a phenolic hydroxy group, in view of the acidity. As the group capable of being converted to a carboxy group, a lactone group may, for example, be considered. As the group capable of being converted to a phenolic hydroxy group, an ether group or a carbonyl group may, for example, be considered.

As the type of the carbon carrier, activated carbon, carbon black or carbon fiber may, for example, be mentioned. Among them, activated carbon is preferred in view of availability and a relatively small number of functional groups present on the surface of the carrier.

As the activated carbon, for example, activated carbon prepared from wood, charcoal, fruit shell such as coconut shell, peat, lignite, coal or the like may be mentioned.

As the shape of the carbon carrier, aggregates of briquette with a length at a level of from 2 to 5 mm, shot at a level of from 4 to 50 mesh or granular charcoal may, for example, be mentioned. Among them, the above aggregates of briquette or shot at a level of from 4 to 20 mesh is preferred.

The specific surface area of the carbon carrier is preferably from 10 to 2,000 $m^2/g$, more preferably from 100 to 1,500 $m^2/g$. When the specific surface area of the carbon carrier is at least the lower limit, the reactivity of the chlorofluoroolefin and hydrogen will further improve, and when it is at most the upper limit, formation of an over-reduced product as a by-product will be further suppressed.

The specific surface area of the carbon carrier is measured by a method in accordance with a gas adsorption method, for example, a BET method.

The amount of the platinum group metal catalyst supported on the carbon carrier is preferably from 0.1 to 10 mass %, more preferably from 0.5 to 1.0 mass % based on the carbon carrier. When the amount of the platinum group metal catalyst supported is at least the lower limit, the reactivity of the chlorofluoroolefin and hydrogen will improve, and when it is at most the upper limit, an excessive temperature increase of the catalyst layer by the heat of reaction will be suppressed and formation of an over-reduced product as a by-product tends to be suppressed and in addition, the catalyst will readily be available.

(Method for Producing Catalyst-Supporting Carrier)

The catalyst-supporting carrier may be produced by a known method. For example, an impregnation method or a colloid method may, for example, be mentioned.

As a method for producing the catalyst-supporting carrier, an impregnation method employing a salt of a metal to be the catalyst is the most common method. For example, a metal salt solution is brought into contact with the carrier to let the metal salt be adsorbed on the surface of the carrier, the carrier is dried, and then a reducing agent is brought into contact with the metal salt on the surface of the carrier to reduce the metal salt to a metal, whereby a metal catalyst-supporting carrier is obtained.

The reducing agent may be a reducing compound such as ammonia or hydrazine, a reducing gas such as hydrogen, an alcohol, an aldehyde, an organic acid or its salt, boron hydride or its salt, or a reducing liquid such as a hydrazine.

The colloid method is a method of making a metal fine particle dispersion be adsorbed on the surface of the carrier, followed by drying to obtain a carrier supporting metal fine particles. The metal fine particle dispersion is obtained by dissolving a metal salt in a solvent and reducing the metal salt by a reducing agent. A polymer organic compound may be used as a protecting agent so as to improve dispersibility of the metal fine particles. A commonly used protecting agent is polyvinylpyrrolidone, polyethyleneimine, polyallylamine, poly(N-carboxymethyl)allylamine, poly(N,N-dicarboxymethyl)allylamine, poly(N-carboxymethyl)ethyleneimine, or the like.

(Reaction)

The reaction may be conducted in a gaseous phase or in a liquid phase so long as the above catalyst is used.

As the reaction method, for example, the following method ($\alpha$) or ($\beta$) may be mentioned depending upon whether the reaction is conducted in a gaseous phase or in a liquid phase. Method ($\alpha$): the chlorofluoroolefin and hydrogen are reacted in a gaseous phase in the presence of the catalyst. Method ($\beta$): the chlorofluoroolefin and hydrogen are reacted in a liquid phase in the presence of the catalyst.

<Method ($\alpha$)>

The method ($\alpha$) may, for example, be a method in which the chlorofluoroolefin and hydrogen are introduced to a reactor packed with the catalyst-supporting carrier and reacted in a gaseous phase. The method may, for example, be specifically a method in which a gas containing a chlorofluoroolefin gas and a hydrogen gas (hereinafter sometimes referred to as "a material mixture gas") is introduced to the reactor, followed by reaction.

The catalyst layer is obtained by packing the reactor with the above-described carbon carrier supporting the platinum group metal catalyst. The packing density of the catalyst-supporting carrier is from 0.5 to 1 $g/cm^3$, more preferably from 0.6 to 0.8 $g/cm^3$. When the packing density is at least the lower limit, the amount of the catalyst-supporting carrier packed per unit volume tends to be large, and the gas amount to be reacted can be increased, whereby the productivity will improve. On the other hand, when it is at most the upper limit, the temperature of the catalyst layer will not be too increased as described above, and the after-described maximum temperature of the catalyst layer tends to be maintained at the desired temperature or below.

As the reactor, a typical flow reactor used for a gas-solid heterogeneous catalytic reaction in which the catalyst-supporting carrier is a solid and the reaction fluid is a gas may be used. Such a flow reactor is roughly classified into a fixed bed reactor and a fluidized bed reactor. The fixed bed reactor is packed with a formed product of the catalyst-supporting carrier so as to reduce the pressure loss of the reaction fluid. Further, a system in which the reactor is packed with the catalyst-supporting carrier in the same manner as the fixed bed reactor, the catalyst-supporting carrier is let to move by gravitation, withdrawn from the bottom of the reactor and regenerated, is called a moving bed reactor.

In the fluidized bed reactor, an operation is carried out such that the catalyst layer behaves as if it is a fluid by the reaction fluid, whereby the catalyst-supporting carrier particles move in the reactor as suspended in the reaction fluid.

In the present invention, either the fixed bed reactor or the fluidized bed reactor may be used, however, in order to suppress deterioration of the catalyst without decreasing the selectivity of the catalytic reaction, the fixed bed reactor capable of properly controlling the reaction temperature is preferred. As the fixed bed reactor, there are a tubular reactor and a tank reactor, and a tubular reactor is preferably used in view of controllability of the reaction temperature. Further, a shell and tube heat exchanger comprising many reaction tubes having a small tube diameter arranged in parallel, and a heating medium circulating over the reaction tubes may, for example, be employed. In a case where more than one reactor is provided in series, more than one catalyst layer is provided.

At least one stage of the catalyst layer is necessary, and two or more stages may be provided.

If the reaction temperature in the catalyst layer decreases, the reactivity of the catalyst decreases. Accordingly, it is preferred to keep the reaction temperature in the catalyst layer to be a desired temperature so as to maintain a high reactivity. In order to keep the reaction temperature in the catalyst layer to be a desired temperature, for example, a method of heating the catalyst layer from outside e.g. by a heat medium may be mentioned.

The chlorofluoroolefin and hydrogen react usually in a part of the region of the catalyst layer (hereinafter referred to as "reaction region"). In a case where the reaction temperature in the catalyst layer is kept to be a desired temperature, usually, the temperature on the upstream side in the reaction zone in the catalyst layer is maintained by heating. In this specification, the temperature on the upstream side in the reaction region maintained by heating will be referred to as "the temperature of the catalyst layer".

The temperature of the catalyst layer is kept to be a temperature higher than the dew point of the material mixture gas in order that the reaction is a gaseous phase reaction.

For example, in a case where CFO-1214ya having a boiling point of 46° C. is used as the chlorofluoroolefin, considering the reactivity, the temperature of the catalyst layer is preferably at least 50° C., more preferably at least 60° C. Further, in a case where HCFO-1224yd having an estimated boiling point of from 15 to 17° C. is used as the chlorofluoroolefin, the temperature of the catalyst layer is preferably at least 20° C., more preferably at least 30° C.

The catalyst usually deteriorates with time as the reaction proceeds. The reaction zone originates from the introduction part of the material mixture gas at the beginning of the reaction. With deterioration of the catalyst at the introduction part of the material mixture gas with time as the reaction proceeds, the reaction zone moves toward the downstream side in the gas flow direction.

Since a high temperature produced gas formed in the reaction zone flows into the vicinity on the downstream side in the reaction zone, the vicinity on the downstream side is usually at the highest temperature in the catalyst layer. In this specification, the temperature of the region at the highest temperature in the catalyst layer will be referred to as "the maximum temperature of the catalyst layer". The temperature on the further downstream side of the vicinity on the downstream side decreases from the maximum temperature of the catalyst layer with an increase of the distance from the reaction zone.

As a method of measuring the maximum temperature of the catalyst layer, for example, a measurement method using a bulk thermometer may be mentioned. As described above, since the reaction zone moves toward the downstream side in the gas flow direction, the region indicating the maximum temperature of the catalyst layer also moves together with the movement of the reaction zone. Accordingly, the measurement part of a bulk thermometer is preliminarily disposed in the gas introduction part of the catalyst layer, and after the beginning of the reaction, the measurement part is moved to the downstream side in the gas flow direction as the reaction proceeds, whereby the maximum temperature of the catalyst layer can be measured.

In this specification, "the gas introduction part" means a point where the material mixture gas is introduced in the catalyst layer.

With a view to suppressing formation of an over-reduced product as a by-product, the reaction is carried out preferably while the maximum temperature of the catalyst layer is controlled to be at most 130° C., more preferably at most 100° C. By controlling the maximum temperature of the catalyst layer to be at most the upper limit, an excess temperature increase of the catalyst layer due to the heat of reaction can be suppressed.

As a method of keeping the maximum temperature of the catalyst layer to be a desired temperature, a method of introducing hydrogen to the catalyst layer dividedly (method ($\alpha$1)) may be mentioned. By the method ($\alpha$1), a high productivity is likely to be maintained while the maximum temperature of the catalyst layer is controlled to be a desired temperature or lower.

In the method ($\alpha$1), the number of hydrogen introduction point is not particularly limited, and may be 2 or more. A case where the number of hydrogen introduction point is 2 may be a case where one point in the gas introduction part from which hydrogen contained in the material mixture gas is introduced and one point from which only a hydrogen gas is introduced (hereinafter referred to as "hydrogen introduction part"), i.e. totally 2 points are provided.

In view of simplification of the process, the number of the hydrogen introduction point is preferably 2. In order that the reaction zone in the catalyst layer can be dispersed without changing the amount of the chlorofluoroolefin introduced, and that generation of the heat of reaction is prevented from being concentrated in one point, whereby local excessive heat generation in the catalyst layer can be suppressed without decreasing the productivity, the number of the hydrogen introduction point is preferably at least 3.

In a case where hydrogen is introduced dividedly, it is preferred to evenly divide and introduce hydrogen to the respective points, whereby the reaction zone is dispersed and the maximum temperature of the catalyst layer is likely to be kept low.

In a case where the hydrogen introduction part is provided, a method ($\alpha$1-1) may be mentioned in which a mixture gas of a part of hydrogen and the entire amount of the chlorofluoroolefin to be introduced to the catalyst layer, as the material mixture gas, is introduced from the gas introduction part (located on the most upstream side in the gas flow direction) of the catalyst layer, and the rest of hydrogen is introduced from at least one hydrogen introduction part on the downstream side of the gas introduction part. By such a method, in addition to the gas flowing from the upstream side (usually the produced gas after a part of the chlorofluoroolefin is reacted with hydrogen), hydrogen is further introduced from the hydrogen introduction part, and this hydrogen reacts with the unreacted chlorofluoroolefin on the downstream side from the hydrogen introduction part. The produced gas after sufficient reaction of the chlorofluoroolefin and hydrogen is discharged from the gas discharge part located on the most downstream side in the gas flow direction of the catalyst layer.

In the method (α1-1), it is preferred that between the gas introduction part and the first hydrogen introduction part, at least part of hydrogen in the material mixture gas is reacted with the chlorofluoroolefin. Further, the hydrogen introduction part on the most downstream side in the gas flow direction is preferably provided at a position such that hydrogen introduced from this hydrogen introduction part can be sufficiently reacted with the unreacted chlorofluoroolefin, in the catalyst layer between this hydrogen introduction part and the gas discharge part.

In a case where at least two catalyst layers are continuously provided in the reactor, as a method of introducing hydrogen, for example, a method may be mentioned in which a part of hydrogen is introduced together with the chlorofluoroolefin from the gas introduction part in the first catalyst layer, and the rest of hydrogen is introduced from the hydrogen filling part of the second or subsequent catalyst layer.

As a method of suppressing the maximum temperature of the catalyst layer to be a desired temperature other than the method (α1), a method (method (α2)) of making an inert gas flow together with the chlorofluoroolefin and hydrogen in the catalyst layer may be mentioned. By making an inert gas flow and controlling the concentrations of the chlorofluoroolefin and hydrogen flowing in the catalyst layer, an excessive temperature increase of the catalyst layer by the heat of reaction can be suppressed. Further, it is possible to use a diluent gas other than the inert gas instead of the inert gas or together with the inert gas.

The inert gas may, for example, be a nitrogen gas, a rare gas or Freon inert to the hydrogenation reaction. The diluent gas other than the inert gas may, for example, be hydrogen chloride.

The amount of the inert gas introduced to the catalyst layer is preferably at least 0.1 mol, more preferably at least 0.5 mol per 1 mol of the chlorofluoroolefin, whereby the maximum temperature of the catalyst layer is likely to be kept low, formation of an over-reduced product as a by-product is likely to be suppressed, and deterioration of the catalyst is likely to be suppressed. The amount of the inert gas introduced is preferably at most 10 mol, more preferably at most 4 mol per 1 mol of the chlorofluoroolefin, in view of the inert gas recovery ratio.

As a method of suppressing the maximum temperature of the catalyst layer to be a desired temperature other than the method (α1) and the method (α2), a method (method (α3)) of adjusting the temperature of a heat medium to heat the reactor to be a lower temperature, setting the dew point of the material mixture gas as the lower limit, may be mentioned. By keeping the temperature of the heat medium low, it is possible to more quickly dissipate the heat of reaction, and an excessive temperature increase of the catalyst layer can be suppressed.

In the method (α3), the lower temperature of the catalyst layer is more advantageous to suppress formation of an over-reduced product which is hardly separated from HFO-1234yf, as a by-product, and accordingly the temperature of the catalyst layer is preferably higher than the dew point and less than 50° C. It is more preferably higher than the dew point and at most 30° C.

To suppress the maximum temperature of the catalyst layer to be a desired temperature, it is preferred to employ the method (α1), (α2) or (α3), or to employ two or three of them in combination.

The reaction pressure is preferably ordinary pressure in view of the handling efficiency.

The contact time of the chlorofluoroolefin gas to the catalyst is preferably from 4 to 60 seconds, more preferably from 8 to 40 seconds. This contact time is the contact time of the chlorofluoroolefin gas as calculated from the amount of the gas introduced to the reactor and the volume of the catalyst layer.

With a view to suppressing formation of an over-reduced product as a by-product, the proportion of hydrogen to the chlorofluoroolefin introduced to the catalyst layer is, as represented by the ratio ($H_2$/Cl) of the total number of moles of hydrogen to the number of moles of chlorine atoms in the chlorofluoroolefin, preferably at most 0.7, more preferably at most 0.6, further preferably at most 0.5. Further, the ratio ($H_2$/Cl) is preferably at least 0.1, more preferably at least 0.2, in view of the yield of the reaction product.

In the method (α), the linear velocity u of the chlorofluoroolefin gas represented by the following formula (9) in the catalyst layer is preferably from 0.1 to 100 cm/sec, more preferably from 1 to 30 cm/sec. This linear velocity u is the linear velocity of the chlorofluoroolefin gas calculated from the amount of the gas introduced to the reactor and the volume of the catalyst layer. When the linear velocity u of the chlorofluoroolefin gas is at least the lower limit, the productivity will improve. When the linear velocity u of the chlorofluoroolefin gas is at most the upper limit, the reactivity of the chlorofluoroolefin and hydrogen will improve.

$$u=(W/100)\times V/S \qquad (9)$$

wherein W is the concentration (mol %) of the chlorofluoroolefin gas in the entire gas flowing in the catalyst layer, V is the flow rate ($cm^3$/sec) of the entire gas flowing in the catalyst layer, and S is the cross-sectional area ($cm^2$) of the catalyst layer relative to the gas flow direction.

As the reactor used in the method (α), a known reactor capable of forming a catalyst layer when packed with the catalyst may be mentioned.

The material of the reactor may, for example, be glass, iron, nickel or an alloy containing any of them as the main component.

The produced gas after the reaction contains, in addition to the aimed hydrofluoroolefin, unreacted material, a reaction intermediate and hydrogen chloride.

Hydrogen chloride contained in the produced gas can be removed by blowing the produced gas into an aqueous alkali solution for neutralization. The alkali in the aqueous alkali solution may, for example, be sodium hydroxide or potassium hydroxide.

As a method for separating the hydrofluoroolefin and the unreacted chlorofluoroolefin from the produced gas, for example, a known method such as distillation may be employed.

The chlorofluoroolefin separated from the produced gas after the reaction can be recycled. For example, separated HCFO-1224yd may be reacted with hydrogen as a chlorofluoroolefin together with CFO-1214ya, or only HCFO-1224yd may be reacted with hydrogen independently from CFO-1214ya.

In a case where a mixture of CFO-1214ya and HCFO-1224yd is used as the chlorofluoroolefin, since HCFO-1224yd is an intermediate when HFO-1234yf is obtained from CFO-1214ya, usually, a mixture with a low proportion of HCFO-1224yd is used. Accordingly, the proportion of HCFO-1224yd based on the total amount of CFO-1214ya and HCFO-1224yd is preferably at most 50 mol %, more preferably at most 25 mol %.

<Method (β)>

In the method (β), a medium is preferably used. The medium may, for example, be water or an organic solvent such as an alcohol.

In a case where a medium is used, the amount of the medium used is preferably from 10 to 100 parts by mass per 100 parts by mass of the chlorofluoroolefin.

As a method of supplying hydrogen, a method of blowing a hydrogen gas to a liquid containing the catalyst-supporting carrier and the chlorofluoroolefin and the medium used as the case requires, or a method of adding a medium having hydrogen preliminarily dissolved by pressurization to a liquid containing the catalyst-supporting carrier and the chlorofluoroolefin may, for example, be mentioned.

The reaction of the chlorofluoroolefin and hydrogen in the method (β) may be conducted by batch or continuously.

The reaction temperature in the method (β) is preferably from 0 to 150° C., more preferably from 20 to 100° C. When the reaction temperature is at least the lower limit, the reactivity of the chlorofluoroolefin and hydrogen will improve. When the reaction temperature is at most 150° C., formation of an over-reduced product as a by-product is likely to be suppressed.

The reaction pressure in the method (β) is preferably from 0.01 to 5 MPaG, more preferably from 0.1 to 1 MPaG by the gauge pressure.

The reaction time in the method (β) is preferably from 1 to 50 hours in the case of the batch reaction, and is preferably from 1 to 60 seconds in the case of the continuous reaction.

The amount of hydrogen supplied in the method (β) is such that the ratio ($H_2/Cl$) of the number of moles of hydrogen supplied to the number of moles of chlorine atoms in the chlorofluoroolefin is preferably at most 0.7, more preferably at most 0.6, further preferably at most 0.5, whereby formation of an over-reduced product as a by-product is likely to be suppressed. Further, the ratio ($H_2/Cl$) is preferably at least 0.1, more preferably at least 0.2, in view of the yield of HFO-1234yf. The amount of hydrogen supplied means the amount of hydrogen dissolved in the reaction liquid.

The reaction liquid after the reaction contains, in addition to the aimed hydrofluoroolefin, unreacted material, a reaction intermediate and hydrogen chloride. Hydrogen chloride contained in the reaction liquid can be removed by neutralization by addition of an alkali to the reaction liquid. The alkali may, for example, be sodium hydroxide or potassium hydroxide.

The alkali may be preliminarily added to the reaction liquid used for the reaction.

As a method of separating the hydrofluoroolefin and the unreacted chlorofluoroolefin from the reaction liquid, for example, a known method such as distillation may be employed.

The chlorofluoroolefin separated from the reaction liquid can be recycled. For example, HCFO-1224yd separated may be reacted with hydrogen as the material chlorofluoroolefin together with CFO-1214ya, or only HCFO-1224yd separated from CFO-1214ya may be reacted with hydrogen.

As the reactor used in the method (β), a known reactor in which the reaction materials can be brought into contact with each other and are subjected to a liquid phase reaction in the presence of the catalyst may be mentioned.

The material of the reactor may, for example, be glass, iron, nickel or an alloy containing any of them as the main component.

[Advantageous Effects]

As described above, by using a platinum group metal catalyst supported on a carbon carrier having a total acidic functional group amount of at most 50 μmol/g, a hydrofluoroolefin can be obtained with formation of an over-reduced product as a by-product suppressed. That is, the platinum group metal catalyst of the present invention has catalytic activity to such an extent that chlorine atoms in the chlorofluoroolefin can be replaced by hydrogen atoms but fluorine atoms cannot be replaced by hydrogen atoms.

By using, as a carrier for the platinum group metal catalyst, a carbon carrier having a reduced total acidic functional group amount, electron donating property of the carbon carrier itself can be reduced. Further, by using such a carbon carrier having low electron donating property, the reducing activity of the platinum group metal supported can be reduced. Such effects by the present invention are estimated as follows. By controlling the ratio of a decrease of the reducing activity by the total acidic functional group amount in the carbon carrier, the hydrogen substitution reaction of the C—Cl bond is let to proceed in priority, and the hydrogen substitution reaction of the C—F bond having a higher binding energy is suppressed.

As described above, according to the production method of the present invention, a high purity hydrofluoroolefin having a low concentration of an over-reduced product can be produced.

EXAMPLES

Now, the present invention will be described in further detail with reference to Examples and Comparative Examples. However, the present invention is by no means restricted to such specific Examples.

Preparation Example 1

Preparation of CFO-1214ya:

CFO-1214ya was prepared by the following method using AK225 as a reaction material.

Into a glass reactor having an internal capacity of 1 L equipped with a Dimroth condenser cooled to 0° C., 3 g of TBAB as a phase transfer catalyst, 83 g (1.485 mol) of potassium hydroxide, 180 g of water and 609 g (3.0 mol) of AK225 were charged, gradually heated with stirring and reacted at 45° C. for 1 hour. Then, a reaction crude liquid separated into an organic phase and an aqueous phase was subjected to liquid separation, and the organic phase was subjected to distillation by a distillation column having a capacity of 1 L and a number of theoretical plate of 10. As a result of distillation, 262 g (1.43 mol) of CFO-1214ya (boiling point: 45° C.) with a purity of 99.5% was obtained.

Example 1

Preparation of HFO-1234yf:

For preparation of HFO-1234yf, a reaction apparatus 101 shown in FIG. 1 was used.

The reaction apparatus 101 comprises two reaction tubes 110A and 110B, and a salt bath 130 in which the tubes are dipped. The reaction tube 110A has two catalyst packing parts 113*a* and 114*a* on the inlet 111*a* side and on the outlet 112*a* side. Likewise, the reaction tube 110B has two catalyst packing parts 113*b* and 114*b* on the inlet 111*b* side and on the outlet 112*b* side. The outlet 112*a* of the reaction tube 110A and the inlet 111*b* of the reaction tube 110B are connected by piping.

As each of the reaction tubes 110A and 110B, a reaction tube made of Inconel (registered trademark) 600 having an inner diameter of 2.54 cm and a length of 100 cm was used. Further, using a palladium catalyst-supporting activated carbon (total acidic functional group amount: 48 μmol/g) having 0.5 part by mass of palladium supported on 100 parts by mass of activated carbon (BET specific surface area: 1,100 m$^2$/g), the catalyst packing part 114a on the outlet 112a side of the reaction tube 110A was packed with the palladium catalyst-supporting activated carbon to form a catalyst layer 112A having a height of 40 cm. Likewise, the catalyst packing parts 113b and 114b on the inlet 111b side and on the outlet 112b side of the reaction tube 110B were respectively packed with the palladium catalyst-supporting activated carbon to form catalyst layers 120B and 120C each having a height of 40 cm. The packing density of the palladium catalyst-supporting activated carbon in each of the catalyst layers 120A to 120C was 0.73 g/cm$^3$.

The total acidic functional group amount in the palladium catalyst-supporting activated carbon is adjusted by subjecting the material palladium catalyst-supporting activated carbon (manufactured by N.E. CHEMCAT Corporation) (total acidic functional group amount: 78 μmol/g) to heat treatment at 400° C. for 3 hours.

The reaction tubes 110A and 110B were dipped in the salt bath 130 so that the catalyst layers 120A to 120C were entirely dipped, and the catalyst layers 120A to 120C were heated to 80° C.

The chlorofluoroolefin gas (A) composed of CFO-1214ya obtained in Preparation Example 1, a hydrogen gas (B) and a nitrogen gas (C) were made to flow through the reaction tubes 110A and 110B so that the total molar ratio would be hydrogen/CFO-1214ya/nitrogen=1/1/2. The contact time of the chlorofluoroolefin gas (A) to the catalyst layers 120A to 120C was 18 seconds, and the linear velocity u of the chlorofluoroolefin gas (A) was 7 cm/sec.

Further, 50% of the hydrogen gas (B) was introduced together with the chlorofluoroolefin gas (A) from the inlet 111a of the reaction tube 110A, and the rest was introduced to a piping portion connecting the reaction tube 110A and the reaction tube 110B. That is, the hydrogen gas (B) was introduced as divided into the catalyst layer 120A (at 0 cm point) and the catalyst layer 120B (at 40 cm point) in a catalyst layer (catalyst layer length: 120 cm) consisting of the catalyst layers 120A to 120C.

The maximum temperatures of the catalyst layers 120A to 120C during the reaction were measured respectively by bulk thermometers 140A to 140C inserted to the respective catalyst layers.

A produced gas (D) discharged from the outlet 112b of the reaction tube 110B of the reaction apparatus 101 was analyzed by gas chromatography (hereinafter referred to as "GC"), whereupon the content of HFO-1243zf based on HFO-1234yf was 510 vol ppm.

Example 2

The reaction was carried out in the same manner as in Example 1 except that as the catalyst-supporting carrier, a palladium catalyst-supporting activated carbon (total acidic functional group amount: 11 μmol/g) having 0.5 part by mass of palladium supported on 100 parts by mass of activated carbon (BET specific surface area: 1,100 m$^2$/g) was used.

The total acidic functional group amount in the palladium catalyst-supporting activated carbon was adjusted by subjecting the material palladium catalyst-supporting activated carbon (manufactured by N.E. CHEMCAT Corporation) (total acidic functional group amount: 78 μmol/g) to heat treatment at 500° C. for 3 hours.

The produced gas (D) was analyzed by GC, whereupon the content of HFO-1243zf based on HFO-1234yf was 27 vol ppm.

Example 3

The reaction was carried out in the same manner as in Example 1 except that as the catalyst-supporting carrier, a palladium catalyst-supporting activated carbon (total acidic functional group amount: 0.8 μmol/g) having 0.5 part by mass of palladium supported on 100 parts by mass of activated carbon (BET specific surface area: 1,100 m$^2$/g) was used.

The total acidic functional group amount in the palladium catalyst-supporting activated carbon was adjusted by subjecting the material palladium catalyst-supporting activated carbon (manufactured by N.E. CHEMCAT Corporation) (total acidic functional group amount: 78 μmol/g) to heat treatment at 600° C. for 3 hours.

The produced gas (D) was analyzed by GC, whereupon the content of HFO-1243zf based on HFO-1234yf was lower than 10 vol ppm (at most the detection limit by GC analysis).

Comparative Example 1

The reaction was carried out in the same manner as in Example 1 except that as the catalyst-supporting carrier, a palladium catalyst-supporting activated carbon (total acidic functional group amount: 78 μmol/g) having 0.5 part by mass of palladium supported on 100 parts by mass of activated carbon (BET specific surface area: 1,100 m$^2$/g) was used.

In this Example, the palladium catalyst-supporting activated carbon (manufactured by N.E. CHEMCAT Corporation) used as the material in Examples 1 to 3 was used without heat treatment.

The produced gas (D) was analyzed by GC, whereupon the content of HFO-1243zf based on HFO-1234yf was 1,220 vol ppm.

Figure 2:
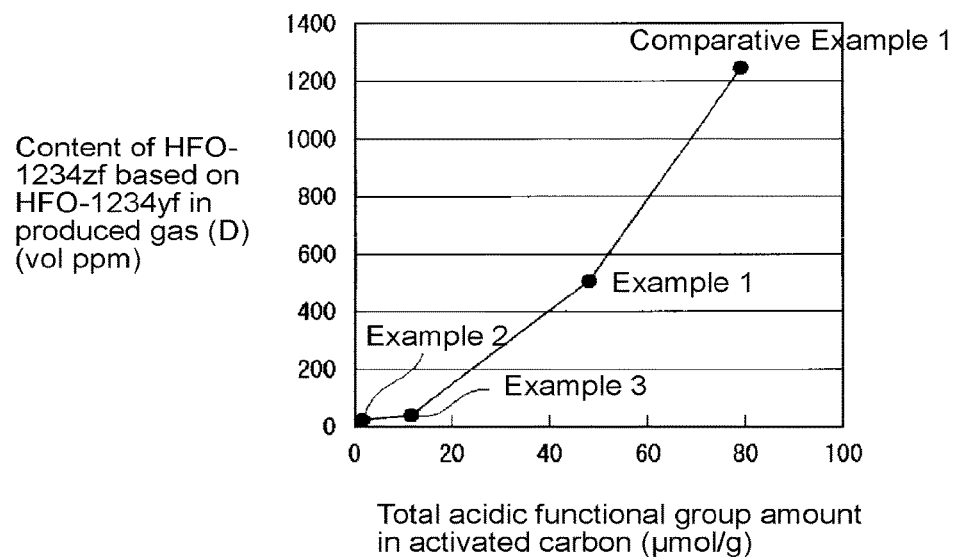
FIG. 2 is a graph illustrating the relation between the total acidic functional group amount in activated carbon and the content of HFO-1243zf based on HFO-1234yf, in Examples 1 to 3 and Comparative Example 1.

The conditions and the content of HFO-1243zf in the produced gas (D) in Examples 1 to 3 and Comparative Example 1 are shown in Table 1. Further, a graph illustrating the relation between the total acidic functional group amount in the activated carbon and the content of HFO-1243zf based on HFO-1234yf in Table 1 is shown in FIG. 2.

TABLE 1

| | | Example 1 | Example 2 | Example 3 | Comparative Example 1 |
|---|---|---|---|---|---|
| Catalyst-supporting carrier | Type of catalyst | Pd | Pd | Pd | Pd |
| | Amount of catalyst supported (part by mass) | 0.5 | 0.5 | 0.5 | 0.5 |
| | Activated carbon (part by mass) | 100 | 100 | 100 | 100 |
| | Total acidic functional group amount in activated carbon (μmol/g) | 48 | 11 | 0.8 | 78 |
| Content of HFO-1243zf based on HFO-1234yf in produced gas (D) (vol ppm) | | 510 | 27 | <10 | 1220 |

Example 4

The reaction was carried out in the same manner as in Example 1 except that as the catalyst-supporting carrier, a palladium/gold alloy catalyst-supporting activated carbon (total acidic functional group amount: 45 µmol/g) having 0.5 part by mass of an alloy of palladium and gold (palladium:gold=90:10 (mass ratio)) supported on 100 parts by mass of activated carbon (BET specific surface area: 1,100 m$^2$/g) was used.

The total acidic functional group amount in the palladium/gold alloy catalyst-supporting activated carbon was adjusted by subjecting the material palladium/gold alloy catalyst-supporting activated carbon (manufactured by N.E. CHEMCAT Corporation) (total acidic functional group amount: 84 µmol/g) to heat treatment at 400° C. for 3 hours.

The produced gas (D) was analyzed by GC, whereupon the content of HFO-1243zf based on HFO-1234yf was 2,917 vol ppm.

Example 5

The reaction was carried out in the same manner as in Example 1 except that as the catalyst-supporting carrier, a palladium/gold alloy catalyst-supporting activated carbon (total acidic functional group amount: 22 µmol/g) having 0.5 part by mass of an alloy of palladium and gold (palladium:gold=90:10 (mass ratio)) supported on 100 parts by mass of activated carbon (BET specific surface area: 1,100 m$^2$/g) was used.

The total acidic functional group amount in the palladium/gold alloy catalyst-supporting activated carbon was adjusted by subjecting the material palladium/gold alloy catalyst-supporting activated carbon (manufactured by N.E. CHEMCAT Corporation) (total acidic functional group amount: 84 µmol/g) to heat treatment at 500° C. for 3 hours.

The produced gas (D) was analyzed by GC, whereupon the content of HFO-1243zf based on HFO-1234yf was 285 vol ppm.

Example 6

The reaction was carried out in the same manner as in Example 1 except that as the catalyst-supporting carrier, a palladium/gold alloy catalyst-supporting activated carbon (total acidic functional group amount: 5 µmol/g) having 0.5 part by mass of an alloy of palladium and gold (palladium:gold=90:10 (mass ratio)) supported on 100 parts by mass of activated carbon (BET specific surface area: 1,100 m$^2$/g) was used.

The total acidic functional group amount in the palladium/gold alloy catalyst-supporting activated carbon was adjusted by subjecting the material palladium/gold alloy catalyst-supporting activated carbon (manufactured by N.E. CHEMCAT Corporation) (total acidic functional group amount: 84 µmol/g) to heat treatment at 600° C. for 3 hours.

The produced gas (D) was analyzed by GC, whereupon the content of HFO-1243zf based on HFO-1234yf was 17 vol ppm.

Comparative Example 2

The reaction was carried out in the same manner as in Example 1 except that as the catalyst-supporting carrier, a palladium/gold alloy catalyst-supporting activated carbon (total acidic functional group amount: 84 µmol/g) having 0.5 part by mass of an alloy of palladium and gold (palladium:gold=90:10 (mass ratio)) supported on 100 parts by mass of activated carbon (BET specific surface area: 1,100 m$^2$/g) was used.

In this Example, the palladium/gold alloy catalyst-supporting activated carbon (manufactured by N.E. CHEMCAT Corporation) used as the material in Examples 4 to 6 was used without heat treatment.

The produced gas (D) was analyzed by GC, whereupon the content of HFO-1243zf based on HFO-1234yf was 8,154 vol ppm.

The conditions and the content of HFO-1243zf in the produced gas (D) in Examples 4 to 6 and Comparative Example 2 are shown in Table 2. Further, a graph illustrating the relation between the total acidic functional group amount in activated carbon and the content of HFO-1243zf based on HFO-1234yf in Table 2 is shown in FIG. 3.

TABLE 2

| | | Example 4 | Example 5 | Example 6 | Comparative Example 2 |
|---|---|---|---|---|---|
| Catalyst-supporting carrier | Type of catalyst | Pd/Au | Pd/Au | Pd/Au | Pd/Au |
| | Amount of catalyst supported (part by mass) | 0.5 | 0.5 | 0.5 | 0.5 |
| | Coconut shell activated carbon (part by mass) | 100 | 100 | 100 | 100 |
| | Total acidic functional group amount in coconut shell activated carbon (µmol/g) | 45 | 22 | 5 | 84 |
| Content of HFO-1243zf based on HFO-1234yf in produced gas (D) (vol ppm) | | 2917 | 285 | 17 | 8154 |

Figure 3:
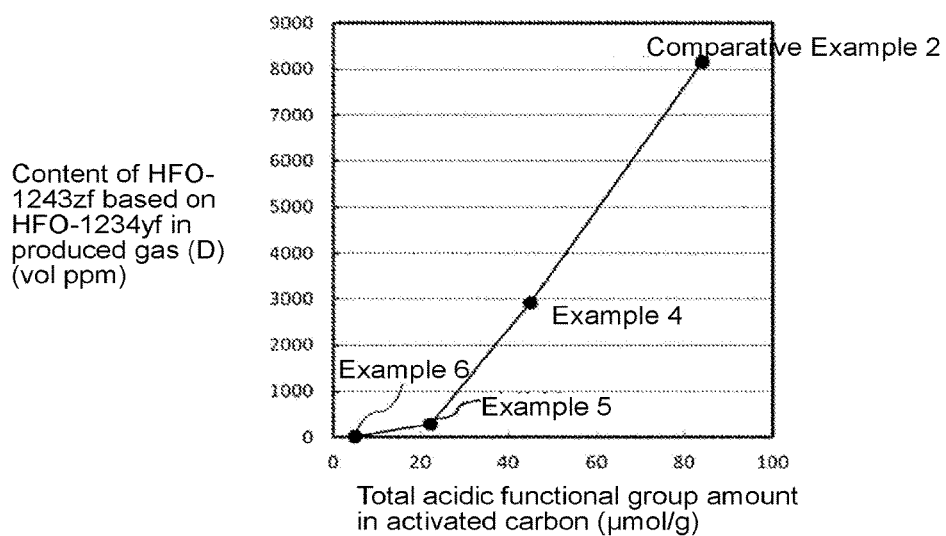
FIG. 3 is a graph illustrating the relation between the total acidic functional group amount in activated carbon and the content of HFO-1243zf based on HFO-1234yf, in Examples 4 to 6 and Comparative Example 2.

As shown in Tables 1 and 2 and FIGS. 2 and 3, in Examples 1 to 6 in which activated carbon having a total acidic functional group amount of at most 50 µmol/g was used as the carrier, the amount of 1243zf which is an over-reduced product formed as a by-product was suppressed as compared with Comparative Examples 1 and 2 in which activated carbon having a total acidic functional group amount exceeding 50 µmol/g was used.

INDUSTRIAL APPLICABILITY

A hydrofluoroolefin obtained by the production method of the present invention has high purity with formation of an over-reduced product as a by-product suppressed. Particularly, HFO-1234yf obtained by the production method of the present invention can be used as e.g. a refrigerant which replaces Freon such as a chlorofluorocarbon without any purification/separation means.

This application is a continuation of PCT Application No. PCT/JP2015/073749 filed on Aug. 24, 2015, which is based upon and claims the benefit of priority from Japanese Patent Application No. 2014-170503 filed on Aug. 25, 2014. The contents of those applications are incorporated herein by reference in their entireties.

REFERENCE SYMBOLS

101: reaction apparatus, 120A to 120C: catalyst layer, A: chlorofluoroolefin gas, B: hydrogen gas, C: nitrogen gas, D: produced gas

What is claimed is:

1. A method for producing a hydrofluoroolefin, the method comprising:

reacting a chlorofluoroolefin of formula (1) with hydrogen in the presence of a platinum group metal catalyst supported on a carbon carrier, to obtain a hydrofluoroolefin of formula (2):

$$CZX=CClY \quad (1)$$

wherein X is a fluorine atom or a chlorine atom, Y is a fluorine atom, a chlorine atom or a hydrogen atom, and Z is a fluorine atom or $CF_3$;

$$CZX'=CHY' \quad (2)$$

wherein X' is a fluorine atom when X is a fluorine atom, or X' is a hydrogen atom when X is a chlorine atom, Y' is a fluorine atom when Y is a fluorine atom, or Y' is a hydrogen atom when Y is a chlorine atom or a hydrogen atom, and Z is the same as Z in the formula (1), wherein the carbon carrier has a total acidic functional group amount of at most 50 μmol/g.

2. The method according to claim 1, wherein the platinum group metal catalyst comprises palladium, a palladium alloy, rhodium or platinum.

3. The method according to claim 1, wherein the platinum group metal catalyst comprises an alloy of a platinum group element and gold.

4. The method according to claim 3, wherein the platinum group metal catalyst comprises an alloy of palladium and gold.

5. The method according to claim 1, wherein the total acidic functional group amount in the carbon carrier is at most 30 μmol/g.

6. The method according to claim 1, wherein the total acidic functional group amount in the carbon carrier is at most 20 μmol/g.

7. The method according to claim 1, wherein the carbon carrier has a specific surface area of from 10 to 2,000 m²/g.

8. The method according to claim 1, wherein an amount of the platinum group metal catalyst is from 0.1 to 10 mass % based on the carbon carrier.

9. The method according to claim 8, wherein the amount of the platinum group metal catalyst is from 0.5 to 1.0 mass % based on the carbon carrier.

10. The method according to claim 1, wherein the chlorofluoroolefin and hydrogen are introduced to a catalyst layer of a tubular reactor packed with the carbon carrier supporting the catalyst, and reacted in a gaseous phase.

11. The method according to claim 10, wherein the tubular reactor has a gas introduction part and a gas discharge part, and the chlorofluoroolefin and hydrogen are introduced to the gas introduction part and hydrogen is introduced from at least one point between the gas introduction part and the gas discharge part.

12. The method according to claim 10, wherein said reacting is carried out while a maximum temperature of the catalyst layer is at most 130° C.

13. The method according to claim 10, wherein a molar ratio of hydrogen to the chlorofluoroolefin introduced to the catalyst layer $[H_2]/[Cl]$ is from 0.1 to 0.7, where $[H_2]$ is total number of moles of hydrogen and $[Cl]$ is number of moles of chlorine atoms in the chlorofluoroolefin.

14. The method according to claim 1, wherein the chlorofluoroolefin and hydrogen are reacted in a liquid phase in the presence of the carbon carrier supporting the catalyst.

15. The method according to claim 1, wherein the chlorofluoroolefin is at least one member selected from the group consisting of chlorotrifluoroethylene, trans-1,2-dichloro-1,2-difluoroethylene, cis-1,2-dichloro-1,2-difluoroethylene, 1,1-dichloro-2,3,3,3-tetrafluoropropene and 1-chloro-2,3,3,3-tetrafluoropropene.

16. The method according to claim 1, wherein the hydrofluoroolefin is 2,3,3,3-tetrafluoropropene and the chlorofluoroolefin is 1,1-dichloro-2,3,3,3-tetrafluoropropene.

17. The method according to claim 1, further comprising:

before said reacting, subjecting the carbon carrier to a heat treatment in an inert gas atmosphere at a temperature of from 350° C. to 1,200° C.

18. The method according to claim 17, wherein the carbon carrier is subjected to the heat treatment after the platinum group metal catalyst is supported.

19. The method according to claim 17, wherein the carbon carrier is subjected to the heat treatment before the platinum group metal catalyst is supported.

* * * * *